(12) United States Patent
Balkus, Jr. et al.

(10) Patent No.: US 9,278,113 B2
(45) Date of Patent: Mar. 8, 2016

(54) TITANIUM DIOXIDE NANOTUBES FOR PRODUCTION AND DELIVERY OF NITRIC OXIDE AND METHODS FOR PRODUCTION THEREOF

(75) Inventors: Kenneth J. Balkus, Jr., The Colony, TX (US); Chalita Ratanatawanate, Dallas, TX (US)

(73) Assignee: THE BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 248 days.

(21) Appl. No.: 12/750,403

(22) Filed: Mar. 30, 2010

(65) Prior Publication Data

US 2010/0247611 A1    Sep. 30, 2010

Related U.S. Application Data

(60) Provisional application No. 61/164,769, filed on Mar. 30, 2009.

(51) Int. Cl.
*A61K 9/70* (2006.01)
*B05D 1/36* (2006.01)
(Continued)

(52) U.S. Cl.
CPC .............. *A61K 33/24* (2013.01); *A61K 33/00* (2013.01); *A61K 41/0042* (2013.01); *A61K 47/48861* (2013.01); *B82Y 5/00* (2013.01); *B82Y 30/00* (2013.01); *C01G 21/21* (2013.01); *C01G 23/047* (2013.01); *C01P 2002/82* (2013.01); *C01P 2004/04* (2013.01); *C01P 2004/13* (2013.01)

(58) Field of Classification Search
CPC .............. A61K 2039/505; A61K 2039/545; A61K 2039/70; A61K 33/00; A61K 33/24
USPC .............. 424/443, 617, 652, 630, 646, 654; 427/2.14; 977/774, 762
See application file for complete search history.

(56) References Cited

U.S. PATENT DOCUMENTS

2004/0158048 A1* 8/2004 Ruane et al. .................. 534/566
2005/0058713 A1* 3/2005 Russell et al. ................. 424/489
(Continued)

OTHER PUBLICATIONS

Ratanatawanate et al., "Fabrication of PbS Quantum Dot Doped TiO2 Nanotubes", ACS Nano, vol. 2, No. 8, 2008, pp. 1682-1688.*
(Continued)

*Primary Examiner* — Ernst V Arnold
*Assistant Examiner* — Hong Yu
(74) *Attorney, Agent, or Firm* — Saliwanchik, Lloyd & Eisenschenk

(57) ABSTRACT

The present disclosure describes compositions operable for releasing nitric oxide under photochemical conditions. The compositions include a titanium dioxide nanomaterial and a nitric oxide-releasing compound deposited on the titanium dioxide nanomaterial that is operable to release nitric oxide under photochemical conditions. Titanium dioxide nanomaterials include, for example, titanium dioxide nanotubes. To facilitate the photochemical release of nitric oxide, some embodiments of the compositions further include a semiconductor that is deposited on the titanium dioxide nanotubes. Both the semiconductor and the nitric oxide-releasing compound may be deposited on the interior surface, exterior surface, or both of the titanium dioxide nanotubes. A polymer may wrap the titanium dioxide nanotubes to protect the nitric oxide-releasing compounds from moisture. Also disclosed herein are methods for producing such compositions and medical devices obtained therefrom.

9 Claims, 6 Drawing Sheets

(51) Int. Cl.
  *A61K 33/24* (2006.01)
  *A61K 33/34* (2006.01)
  *A61K 33/26* (2006.01)
  *A61K 33/00* (2006.01)
  *A61K 41/00* (2006.01)
  *A61K 47/48* (2006.01)
  *B82Y 5/00* (2011.01)
  *B82Y 30/00* (2011.01)
  *C01G 21/21* (2006.01)
  *C01G 23/047* (2006.01)

(56) References Cited

U.S. PATENT DOCUMENTS

2006/0178445 A1* 8/2006 Mcintyre et al. ............... 523/122
2008/0175881 A1* 7/2008 Ippoliti et al. ................. 424/423
2008/0216891 A1* 9/2008 Harkness et al. ............. 136/256

OTHER PUBLICATIONS

Du et al., "Preparation and structure analysis of titanium oxide nanotubes", Applied Physics Letters, 2001, 79, 3702-3704.*

Incoming Sunlight: retrieved from internet: http://earthobservatory.nasa.gov/Features/EnergyBalance/page2.php. Retrieved on Mar. 10, 2014.*

Kim et al.: Enhanced photocatalytic activity in composites of TiO2 nanotubes and CdS nanoparticles, Chemical Communication, The Royal Society of Chemistry, 2006, pp. 5024-5026).*

Vogel et al.: Quantum-sized PbS, CdS, Ag2S, Sb2S3, and Bi2S3 particles as sensitizers for various nanoporous wide-bandgap semiconductors, American Chemical Society, 1994, 98, pp. 3183-3188.*

Cho et al.: Therapeutic nanoparticles for drug delivery in cancer, Review, Clin Cancer Res, Mar. 1, 2008, 14(5), pp. 1310.*

* cited by examiner

US 9,278,113 B2

TITANIUM DIOXIDE NANOTUBES FOR PRODUCTION AND DELIVERY OF NITRIC OXIDE AND METHODS FOR PRODUCTION THEREOF

CROSS-REFERENCE TO RELATED APPLICATIONS

This application claims priority to U.S. provisional patent application 61/164,769, filed Mar. 30, 2009, which is incorporated by reference herein in its entirety.

STATEMENT REGARDING FEDERALLY SPONSORED RESEARCH

Not applicable.

BACKGROUND

Nitric oxide (NO) is an endogenous mediator of various physiological functions in the gastrointestinal, genitourinary, cardiovascular, respiratory, and nervous systems. Nitric oxide has long been established as a signaling molecule that promotes relaxation of smooth muscle cells. More recently, it has been established or implicated that NO can mediate other biological processes and diseases including, for example, wound healing, inflammation, plant disease resistance, sexual dysfunction, social dysfunction, cancer, coronary heart disease, restenosis, hypertension and angiogensis. There are also implications of the role of NO in organ perseveration during transplantation and procurement. The implication of NO in so many biological processes and diseases has stimulated interest in its exogenous delivery. However, NO is a diatomic free radical, and its exogenous delivery as a gas to biological systems has proved impractical due to its high reactivity.

A number of systems have been proposed and tested for in situ generation and delivery of NO. Such NO-releasing compounds include chemical compounds such as, for example, diazeniumdiolates, S-nitrosothiols, metal nitrosyl complexes, NO-releasing gold nanoparticles, NO-releasing polyethyleneimine (PEI) fibers and NO-releasing zeolites. For some NO-releasing compounds, the rate of NO release can be varied somewhat through temperature, pH or enzymatic control, although most NO-releasing compounds are non-specific and release NO spontaneously. Poor solubility and generation of potentially toxic byproducts have further stalled the use of NO-releasing compounds for exogenous delivery of NO.

In view of the foregoing, compositions and methods providing for controlled or sustained release of NO would be of substantial benefit in the art. Desirably, such systems would promote controlled or sustained release of NO to exploit the beneficial properties of NO in biological systems, while at the same time minimizing the toxicity or biological incompatibility of present NO-releasing materials.

SUMMARY

In various embodiments, the present disclosure describes compositions operable for release of nitric oxide under photochemical conditions. The compositions include a titanium dioxide nanomaterial and a nitric oxide-releasing compound deposited on the titanium dioxide nanomaterial. The nitric oxide-releasing compound is operable to release nitric oxide under photochemical conditions.

In other various embodiments, compositions operable for photochemical release of nitric oxide include titanium dioxide nanotubes, a nitric oxide-releasing compound deposited on the titanium dioxide nanotubes, a semiconducting quantum dot material deposited on the titanium dioxide nanotubes, and a polymer wrapping the titanium dioxide nanotubes. The nitric oxide-releasing compound is operable to release nitric oxide under photochemical conditions.

In other various embodiments, methods described herein include: providing titanium dioxide nanotubes, depositing a nitric oxide-releasing compound on the titanium dioxide nanotubes and depositing a semiconducting quantum dot material on the titanium dioxide nanotubes. The nitric oxide-releasing compound is operable to release nitric oxide under photochemical conditions. At least a portion of the nitric oxide-releasing compound and at least a portion of the semiconducting quantum dot material are deposited on the exterior surface of the titanium dioxide nanotubes.

In still other various embodiments, methods described herein include: providing titanium dioxide nanotubes, wrapping the titanium dioxide nanotubes with a cationic surfactant, depositing a nitric oxide-releasing compound on the titanium dioxide nanotubes and depositing a semiconducting quantum dot material on the titanium dioxide nanotubes. The nitric oxide-releasing compound is operable to release nitric oxide under photochemical conditions. The nitric oxide-releasing compound and the semiconducting quantum dot material are deposited on the interior surface of the titanium dioxide nanotubes.

The foregoing has outlined rather broadly the features of the present disclosure in order that the detailed description that follows may be better understood. Additional features and advantages of the disclosure will be described hereinafter, which form the subject of the claims.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein.

DETAILED DESCRIPTION

Figure 1:
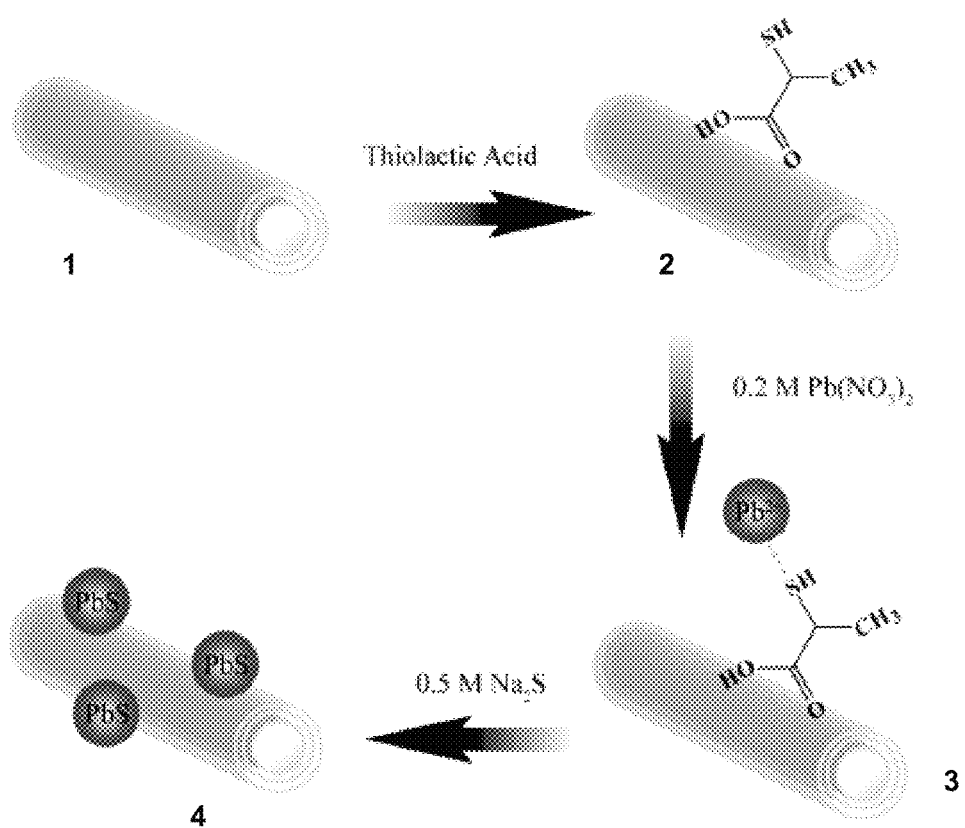
FIG. 1 shows an illustrative process through which PbS quantum dots may be deposited on titanium dioxide nanotubes.

In the following description, certain details are set forth such as specific quantities, sizes, etc. so as to provide a thorough understanding of the present embodiments disclosed herein. However, it will be evident to those of ordinary skill in the art that the present disclosure may be practiced without such specific details. In many cases, details concerning such considerations and the like have been omitted inasmuch as such details are not necessary to obtain a complete understanding of the present disclosure and are within the skills of persons of ordinary skill in the relevant art.

Referring to the drawings in general, it will be understood that the illustrations are for the purpose of describing particular embodiments of the disclosure and are not intended to be limiting thereto. Drawings are not necessarily to scale.

While most of the terms used herein will be recognizable to those of ordinary skill in the art, it should be understood, however, that when not explicitly defined, terms should be interpreted as adopting a meaning presently accepted by those of ordinary skill in the art. In cases where the construction of a term would render it meaningless or essentially meaningless, the definition should be taken from Webster's Dictionary, 3rd Edition, 2009. Definitions and/or interpretations should not be incorporated from other patent applications, patents, or publications, related or not, unless specifically stated in this specification or if the incorporation is necessary for maintaining validity.

As used herein, the term "nitric oxide-releasing compound" refers to, for example, a compound that releases nitric oxide through a chemical reaction upon exposure to specified conditions.

As used herein, the term "quantum dot material" refers to, for example, a semiconducting material whose excitons are confined in all three spatial dimensions. In such quantum dot materials, the conduction characteristics are directly related to the size and shape of the individual particles. Typically, the smaller the particle size, the larger the semiconducting band gap.

As used herein, the term "medical device" refers to, for example, any device used either internally or externally for treating, mediating, curing or alleviating a condition in a patient or any device used as part of a medical procedure.

Mammalian cells synthesize NO using a two-step enzymatic process that oxidizes L-arginine to N-omega-hydroxy-L-arginine, which is subsequently converted into L-citrulline and an uncharged NO free radical. Three different nitric oxide synthase enzymes regulate NO production. Neuronal nitric oxide synthase (NOS1 or nNOS) is formed within neuronal tissue and plays a role in neurotransmission. Endothelial nitric oxide synthase (NOS3 or eNOS) is secreted by endothelial cells and induces vasodilatation. Inducible nitric oxide synthase (NOS2 or iNOS) is principally found in macrophages, hepatocytes and chondrocytes and is associated with immune cytotoxicity. Neuronal NOS and eNOS are constitutive enzymes that regulate the rapid, short-term release of small amounts of NO. In these minute amounts NO activates guanylate cyclase, which elevates cyclic guanosine monophosphate (cGMP) concentrations, which in turn increase intracellular $Ca^{2+}$ levels. Increased intracellular $Ca^{3+}$ levels result in smooth muscle relaxation and vasodilation effects. Inducible NOS is responsible for the sustained release of larger amounts of NO and is activated by extracellular factors including endotoxins and cytokines. These higher NO levels play a role in cellular immunity.

Nitric oxide's therapeutic potential has been studied in a number of diverse clinical indications including, for example, cancer, coronary artery heart disease, restenosis, hypertension, angiogenesis, sexual dysfunction and social dysfunction. Moreover, recent studies have demonstrated that NO also possesses considerable in vivo and ex vivo antimicrobial activity, suggesting a possible role in treating infectious diseases and fungal infections. The role of NO in wound healing and general inflammation has also been studied.

Another postulated clinical role of NO is in the field of organ transplantation, particularly heart transplantation. One of the major factors in realizing a successful heart transplantation is adequate organ preservation during the procurement, storage, and implantation stages of a transplant. Currently, organ preservation is based on a single flush induction of cardioplegia and hypothermic storage in a solution. While this method is effective, time is still the major factor in healing, because the heart can only tolerate 4-5 hours of ischemia. Prolonged periods of ischemia lead to increased acute and chronic organ failure due to vasoconstriction and endothelium damage of the arteries upon a decrease in NO production.

Attempts to mimic the natural release of NO produced by NOS enzymes have yet to be successful. Embodiments of the present disclosure seek to provide compositions permitting the controlled or sustained release of NO, either in vivo or ex vivo. Controlled or sustained release of NO is accomplished by utilizing nitric oxide-releasing compounds that do not release NO until an activation event occurs to stimulate NO release. Nitric oxide release may occur, for example, through photochemical activation. Such compositions may be substantially non-toxic to biological systems and/or successfully mimic the natural enzymatic release of NO. In view of the established role of NO in so many biological processes, such compositions would undoubtedly demonstrate substantial utility in the art. Medical and therapeutic devices that contain such compositions are also contemplated herein.

To mitigate the potential toxicity of some nitric oxide-releasing compounds, the nitric oxide-releasing compounds may be deposited on a surface. Surfaces may include metal oxide surfaces in some embodiments. In some embodiments, the metal oxide surface may itself be photoactive to assist in the photochemical activation of the nitric oxide-releasing compounds within the compositions. For example, in some embodiments, the metal oxide surface may be titanium dioxide ($TiO_2$), which is a well-studied material for photocatalysis. The titanium dioxide may take the form of a nanoscale material such as, for example, nanofibers, nanorods or nanotubes in order to provide a high surface to volume ratio beneficial for photocatalysis.

In various embodiments, the present disclosure describes compositions operable for release of nitric oxide under photochemical conditions. The compositions include a titanium dioxide nanomaterial and a nitric oxide-releasing compound deposited on the titanium dioxide nanomaterial. The nitric oxide-releasing compound is operable to release nitric oxide under photochemical conditions. In some embodiments, the titanium dioxide nanomaterial is titanium dioxide nanotubes.

Nitric oxide-releasing compounds that produce nitric oxide through a chemical reaction may be considered nitric oxide prodrugs. Nitric oxide-releasing compounds may include, for example, organic N-nitro and N-nitroso compounds (for example, diazeniumdiolates), organic O-nitro and O-nitroso compounds (for example, glyceryl trinitrate and amyl nitrite), organic C-nitro and C-nitroso compounds (for example, nitrolipids, nitronic acids, nitroalkanes, diazetine dioxides and furoxans), S-nitrosophenols, S-nitrosothiols, N-hydroxyurea and derivatives, N-hydroxyguanidine and derivatives, and nitroprusside ion and other metal nitrosyl complexes. Among these nitric oxide-releasing compounds, diazeniumdiolates, S-nitrosothiols and metal nitrosyl complexes are among the most studied for photochemical activation to affect NO release. Although the embodiments and examples referenced hereinafter have been centered on photochemically-active diazeniumdiolates, S-nitrosothiols and metal nitrosyl complexes, one of ordinary skill in the art will recognize that any nitric oxide-releasing compound that is photochemically active may be used to operate within the spirit and scope of the present disclosure.

The general structural formula of diazeniumdiolates is exemplified by structure I below, where R and R' are independently H or any alkyl, alkenyl, alkynyl, aryl, aralkyl, alkaryl group or substituted derivative thereof. Charge balance is generally affected by a monovalent cation such as, for example, a $Na^+$ cation. Diazeniumdiolates are typically formed by exposing an amine to nitric oxide gas.

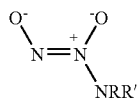

I

The structure of S-nitrosothiols is exemplified by structure II below. R is any alkyl, alkenyl, alkynyl, aryl, aralkyl, alkaryl group or substituted derivative thereof. Like diazeniumdiolates, S-nitrosothiols are typically formed by exposing a thiol to nitric oxide gas.

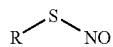

II

Metal nitrosyl complexes typically include at least one to about 6 nitrosyl ligands coordinated to a metal center. The metal center may include, for example, transition metals, lanthanide metals and actinide metals. In some embodiments of the present disclosure, the metal nitrosyl complex is a ruthenium nitrosyl complex.

Depending on the band gap, photochemical conditions for stimulating nitric oxide release from the compositions described herein may involve irradiating the nitric oxide-releasing compounds with a light source such as, for example, visible light, ultraviolet light, near infrared light, infrared light and various combinations thereof. In various embodiments, inclusion of a semiconductor material, such as a quantum dot material, as part of the compositions may lower the band gap into a lower energy portion of the electromagnetic spectrum. Particularly for biological applications, it may be advantageous adjust the band gap into the near-infrared region of the electromagnetic spectrum (~700 nm-1400 nm) for stimulating NO release. Various tissue chloroplasma in the human body block light penetration except for a narrow region of about 700 nm to about 1100 nm in the near infrared region of the electromagnetic spectrum. By selectively adjusting the band gap through inclusion of a semiconductor material in the compositions of the present disclosure, the compositions may be designed for in vivo photochemical release of NO using a wavelength of light that is not absorbed by the body.

In some embodiments, photochemical activation of the nitric oxide-releasing compound may not require accessing a lower energy region of the electromagnetic spectrum, and photochemical conditions for activating the nitric oxide-releasing compound may involve the use of an ultraviolet light source. In such embodiments, non-limiting nitric oxide-releasing compounds may include, for example, diazeniumdiolates, S-nitrosothiols and metal nitrosyl complexes.

In some embodiments, compositions of the present disclosure further include a semiconductor material deposited on the titanium dioxide nanotubes. In some embodiments, the semiconductor material is PbS. In general, the semiconductor material may include nanoparticles such as, for example, PbS, PbSe, CuS, $Cu_2S$, $FeS_2$, CdS, CdSe, CdTe, ZnS, $Ag_2S$, $CuInS_2$, $Rh_2S_3$ and $RuS_2$. Such nanoparticles and others may be quantum dot materials in some embodiments. In some embodiments, the quantum dot material may be used to narrow the band gap for absorption of electromagnetic radiation, thereby facilitating the photochemical activation of the nitric oxide-releasing compounds in the present compositions. Further, by narrowing the band gap, the absorption of electromagnetic radiation may be changed into a less energetic and more generally usable region of the electromagnetic spectrum, particularly for in vivo applications.

Lead sulfide (PbS) is a semiconductor material that may have particular utility in the compositions of the present disclosure. This semiconductor material has a small band gap of about 0.41 eV and a large exciton Bohr radius of about 20 nm. PbS quantum dot materials may further improve upon these properties due to multiple exciton generation and efficient spatial separation of photogenerated charge, thereby preventing electron-hole recombination. Further, the band gap of PbS quantum dots may be adjusted by varying the size of the quantum dot materials. For example, for PbS quantum dots having diameters between about 2 nm and about 9 nm, the band gap may be tuned in the range of 0.83 eV to 2.34 eV.

Titanium dioxide nanotubes generally have outer diameters ranging from about 10 nm to about 20 nm and inner diameters ranging from about 5 nm to about 10 nm. Lengths of the titanium dioxide nanotubes may be up to about 1 μm. Both the interior and exterior surfaces of the titanium dioxide nanotubes may be modified with nitric oxide-releasing compounds and semiconductor materials, as described hereinafter.

In some embodiments, at least a portion of the semiconductor material is deposited on the exterior surface of the titanium dioxide nanotubes. In some or other embodiments, at least a portion of the nitric oxide-releasing compound is deposited on the exterior surface of the titanium dioxide nanotubes. In some embodiments, both the interior surface and exterior surface of the titanium dioxide nanotubes contain the semiconductor material In some or other embodiments, both the interior surface and exterior surface of the titanium dioxide nanotubes contain the nitric oxide-releasing compound. In some embodiments, the semiconductor material is deposited on the interior surface of the titanium dioxide nanotubes. In some or other embodiments, the nitric oxide-releasing compound is deposited on the interior surface of the titanium dioxide nanotubes. Deposition of the semiconductor material and the nitric oxide-releasing compound may be conducted independently of one another, such that one component is deposited on the exterior surface of the titanium dioxide nanotubes and one component is deposited on the interior surface of the titanium dioxide nanotubes.

In some embodiments, at least one of the nitric oxide-releasing compound and the semiconductor material are covalently bound to the titanium dioxide nanotubes. In some or other embodiments, the nitric oxide-releasing compound is covalently bound to the titanium dioxide nanotubes. In some or other embodiments, the semiconductor material is covalently bound to the titanium dioxide nanotubes. In some embodiments, the nitric oxide-releasing compound is adsorbed to the titanium dioxide nanotubes. In some embodiments, the semiconductor material is adsorbed to the titanium dioxide nanotubes. In an embodiment, adsorption of the nitric oxide-releasing compound or the semiconductor material takes place through a carboxyl group adsorbed on the titanium dioxide nanotube surface.

In some embodiments, compositions of the present disclosure further include a polymer wrapping the titanium dioxide nanotubes. In some embodiments, the polymer is a water-soluble polymer. Water-soluble polymers include, for example, poly-L-arginine, poly(vinyl pyrrolidone), poly(ethylene oxide), poly(acrylic acid), and poly(vinyl alcohol). However, one of ordinary skill in the art will recognize that other water-soluble polymers are known and may be used equivalently within the spirit and scope of the present disclosure. Such water-soluble polymers may make the present compositions water-soluble and facilitate the transport of the compositions across cell membranes. Further, the polymer may protect the nitric oxide-releasing compounds of the compositions from moisture, thereby leaving them in an unactivated form for photochemical release of NO, rather than producing indiscriminate NO release mediated by water.

In some embodiments of the present disclosure, compositions operable for photochemical release of nitric oxide include titanium dioxide nanotubes, a nitric oxide-releasing compound deposited on the titanium dioxide nanotubes, a semiconducting quantum dot material deposited on the titanium dioxide nanotubes, and a polymer wrapping the titanium dioxide nanotubes. The nitric oxide-releasing compound is operable to release nitric oxide under photochemical conditions. In some embodiments, the polymer is a water-soluble polymer such as, for example, poly-L-arginine. In an embodiment, the polymer protects the nitric oxide-releasing compound from moisture.

In some embodiments of the compositions, at least a portion of the semiconducting quantum dot material is deposited on the exterior surface of the titanium dioxide nanotubes. In some or other embodiments, at least a portion of the nitric oxide-releasing compound is deposited on the exterior surface of the titanium dioxide nanotubes. In some embodiments, both the interior surface and exterior surface of the titanium dioxide nanotubes contain the semiconducting quantum dot material. In some or other embodiments, both the interior surface and exterior surface of the titanium dioxide nanotubes contain the nitric oxide-releasing compound. In some embodiments, the semiconducting quantum dot material is deposited on the interior surface of the titanium dioxide nanotubes. In some or other embodiments, the nitric oxide-releasing compound is deposited on the interior surface of the titanium dioxide nanotubes. In some embodiments, at least one of the nitric oxide-releasing compound and the semiconducting quantum dot material are covalently bound to the titanium dioxide nanotubes.

In some embodiments, compositions of the present disclosure further include a tissue-targeting moiety deposited on the exterior surface of the titanium dioxide nanotubes. In some embodiments, the tissue-targeting moiety may be covalently bonded to the exterior surface of the titanium dioxide nanotubes. Illustrative tissue-targeting moieties include, for example, antibodies, peptides, DNA, RNA and the like.

In other various embodiments, the present disclosure describes methods for producing compositions operable for releasing nitric oxide under photochemical conditions.

In some embodiments, the methods described herein include: providing titanium dioxide nanotubes, depositing a nitric oxide-releasing compound on the titanium dioxide nanotubes and depositing a semiconducting quantum dot material on the titanium dioxide nanotubes. The nitric oxide-releasing compound is operable to release nitric oxide under photochemical conditions. At least a portion of the nitric oxide-releasing compound and at least a portion of the semiconducting quantum dot material are deposited on the exterior surface of the titanium dioxide nanotubes.

In other embodiments, the methods described herein include: providing titanium dioxide nanotubes, wrapping the titanium dioxide nanotubes with a cationic surfactant, depositing a nitric oxide-releasing compound on the titanium dioxide nanotubes and depositing a semiconducting quantum dot material on the titanium dioxide nanotubes. The nitric oxide-releasing compound is operable to release nitric oxide under photochemical conditions. The nitric oxide-releasing compound and the semiconducting quantum dot material are deposited on the interior surface of the titanium dioxide nanotubes.

In still other embodiments, the methods described herein include: providing titanium dioxide nanotubes, wrapping the titanium dioxide nanotubes with a cationic surfactant, depositing a nitric oxide-releasing compound on the titanium dioxide nanotubes and depositing a semiconducting quantum dot material on the titanium dioxide nanotubes. The nitric oxide-releasing compound is operable to release nitric oxide under photochemical conditions. At least the semiconducting quantum dot material is deposited on the interior surface of the titanium dioxide nanotubes.

In some embodiments of the methods, at least one of the nitric oxide-releasing compound and the semiconducting quantum dot material are covalently bound to the titanium dioxide nanotubes. In some embodiments, the methods further include wrapping the titanium dioxide nanotubes with a polymer such as, for example, a water-soluble polymer.

In various embodiments, the nitric oxide-releasing compounds and the semiconducting quantum dot materials may be selectively deposited on only the interior surface or the exterior surface of the titanium dioxide nanotubes. In various embodiments, the methods of the present disclosure further include wrapping the exterior surface of the titanium dioxide nanotubes with a cationic surfactant, followed by deposition of the nitric oxide-releasing compounds and/or the semiconducting quantum dot materials on the interior surface of the titanium dioxide nanotubes. When the exterior surface of the titanium dioxide nanotubes is blocked with a cationic surfactant, deposition takes place on the interior surface of the titanium dioxide nanotubes. When the exterior surface of the titanium dioxide nanotubes is not blocked with a cationic surfactant, deposition may take place either on the exterior surface or a combination of the interior surface and the exterior surface. In light of the present disclosure, one of ordinary skill in the art will recognize that any of the various embodiments described herein having a particular location for either of the nitric oxide-releasing compounds and/or the semiconducting quantum dot materials may be conducted equivalently through routine experimental modification to locate these moieties at a different location on either the interior surface or the exterior surface of the titanium dioxide nanotubes.

Compositions of the present disclosure may be included with medical devices. In some embodiments, the compositions may coat the surface of the medical device. The medical devices of the present disclosure may be manufactured from a material such as, for example, metal, glass, ceramic, fabrics and polymers upon which the compositions described herein may be deposited.

Medical devices of the present disclosure include stents, vascular grafts, pacemaker leads, heart valves, electrodes, sensors, trocars, guide wires, catheters, ocular lenses, sling materials, sutures, wound dressings and bandages, blood collection bags and storage tubes, tubing for blood transfusions and hemodialysis. In some embodiments, the medical devices are used internally. Medical devices of the present disclosure may be used to treat, mediate or prevent a variety of diseases in which nitric oxide is implicated as having a functional role. Such diseases include, for example, infection, diabetic neuropathy, hypertension, sexual dysfunction, cancer, deep vein thrombosis, tendinopathy, and Duchenne muscular dystrophy. In some embodiments, the compositions and medical devices of the present disclosure may replace or be used in combination with traditional anti-coagulant drugs and therapies.

In some embodiments, the compositions of the present disclosure may be formulated into a cream or lotion. Such creams and lotions may be used to increase circulation in diabetic and other circulation-deficient patients. The creams and lotions may also be applied to the scalp as a hair growth treatment. A patient need only apply the cream or lotion and then expose themselves to a light source or ambient room lighting to experience a therapeutic effect from photo-released NO.

EXPERIMENTAL EXAMPLES

The following examples are provided to more fully illustrate some of the embodiments disclosed hereinabove. It should be appreciated by those of ordinary skill in the art that the techniques disclosed in the examples that follow represent techniques that constitute illustrative modes for practice of the disclosure. Those of ordinary skill in the art should, in light of the present disclosure, appreciate that many changes can be made in the specific embodiments that are disclosed and still obtain a like or similar result without departing from the spirit and scope of the disclosure.

Example 1

Synthesis of Titanium Dioxide Nanotubes

P25 titanium dioxide was dissolved in sodium hydroxide solution to form sodium titanate sheets. The solution containing sodium titanate sheets was then treated with acid and annealed to form titanium dioxide nanotubes.

Example 2

Deposition of PbS Quantum Dots on Titanium Dioxide Nanotubes

FIG. 1 shows an illustrative process through which PbS quantum dots may be deposited on titanium dioxide nanotubes. Titanium dioxide nanotubes 1 were exposed to thiolactic acid in solution, thereby resulting in adsorption of thiolactic acid on the surface of thiol-tethered titanium dioxide nanotube 2. Exposure of thiol-tethered titanium dioxide nanotube 2 to a 0.2 M solution of $Pb(NO_3)_2$ resulted in coordination of $Pb^{2+}$ to the free thiol in 2 to produce $Pb^{2+}$-tethered titanium dioxide nanotube 3. Exposure of 3 to a 0.5 M solution of $Na_2S$ resulted in the precipitation of the $Pb^{2+}$ cation as PbS quantum dots in PbS quantum dot titanium dioxide nanotube 4. In PbS quantum dot titanium dioxide nanotube 4, the structure of the thiolactic acid moiety has been omitted for clarity.

Figure 2A:
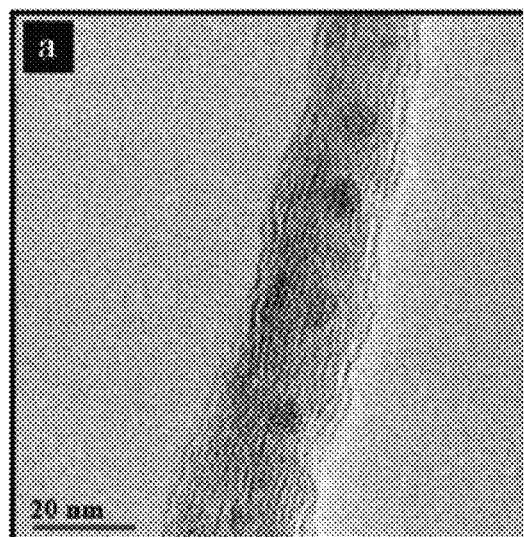
FIGS. 2A and 2B show illustrative TEM images of PbS quantum dots deposited on the interior surface of titanium dioxide nanotubes.
Figure 2B:
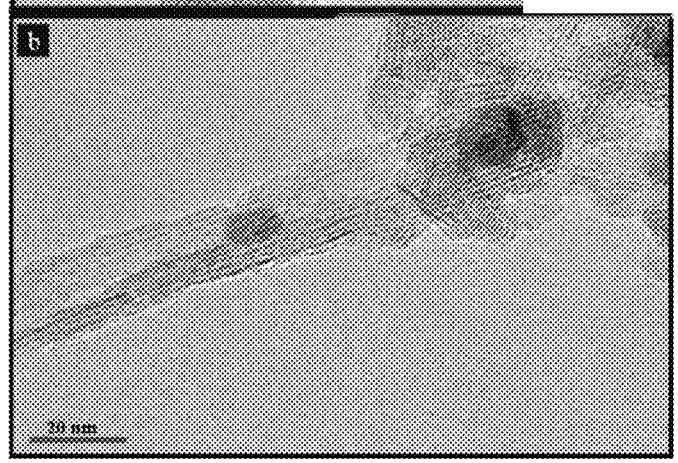

The embodiment shown in FIG. 1 demonstrates the deposition of the PbS quantum dots on the exterior surface of the titanium dioxide nanotubes. However, by first blocking the outer surface of the titanium dioxide nanotubes with a cationic surfactant (e.g., tetraalkylammonium salts) before following the procedure outlined in FIG. 1, the PbS quantum dots were instead deposited on the interior surface of the titanium dioxide nanotubes. FIGS. 2A and 2B show illustrative TEM images of PbS quantum dots deposited on the interior surface of titanium dioxide nanotubes.

Figure 3:
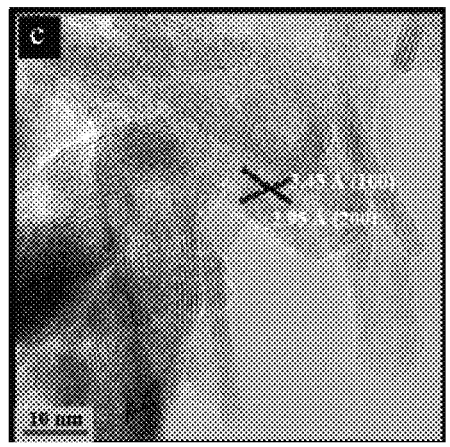
FIG. 3 shows an illustrative TEM image showing PbS nanorods within the interior of titanium dioxide nanotubes.

The titanium dioxide nanotubes containing PbS quantum dots deposited on the interior surface were thermally stable upon annealing at 500° C. in Ar atmosphere, except for sintering of the PbS quantum dots into PbS nanorods contained within the titanium dioxide nanotubes. FIG. 3 shows an illustrative TEM image showing PbS nanorods within the interior of titanium dioxide nanotubes. The length of the PbS nanorods was estimated to be about 25 nm. Another significant outcome of annealing was that the titanium dioxide nanotubes were thermally stable and did not collapse or unroll upon heating, as occurs in the absence of PbS quantum dots. Therefore, it can be inferred that the PbS quantum dots deposited on the interior surface of the titanium dioxide nanotubes conferred additional stability to the titanium dioxide nanotubes themselves.

Example 3

Figure 4:
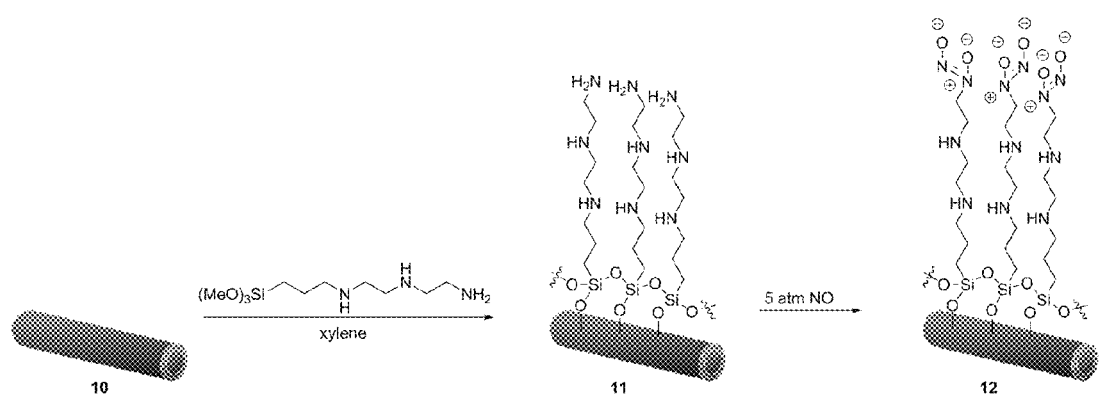
FIG. 4 shows a schematic of an illustrative synthesis of diazeniumdiolate-modified titanium dioxide nanotubes.

Synthesis and NO Release of Diazeniumdiolate-Modified Titanium Dioxide Nanotubes FIG. 4 shows a schematic of an illustrative synthesis of diazeniumdiolate-modified titanium dioxide nanotubes 12. Titanium dioxide nanotubes 10 were suspended in xylene solvent, and an organosilanol linker species was added. The silanol moieties were hydrolyzed upon treatment, and a covalent bond formed to link the silane to the titanium dioxide nanotubes through a silicon-oxygen covalent bond. Next, the silane-functionalized titanium dioxide nanotubes 11 were exposed to 5 atm of NO gas to form diazeniumdiolate-modified titanium dioxide nanotubes 12. A number of organosilanol linker species similar to that shown in FIG. 4 are commercially available and could be used equivalently to bond to the titanium dioxide nanotubes.

Figure 5:
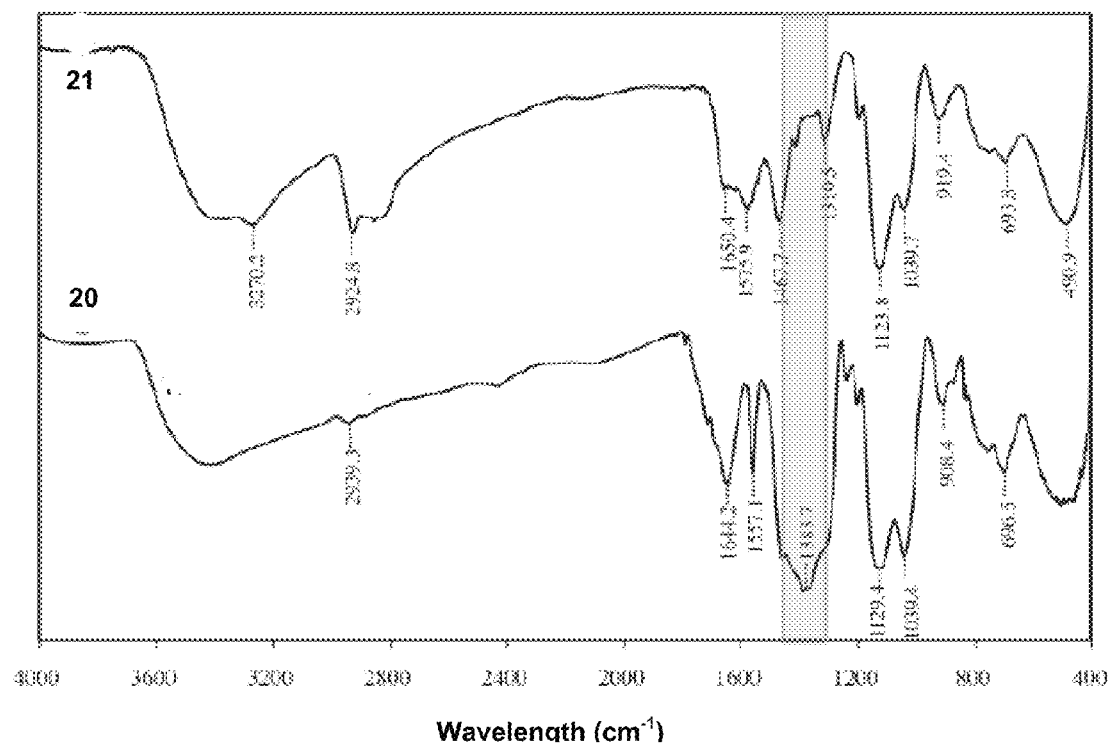
FIG. 5 shows illustrative comparative FTIR spectra of diazeniumdiolate-modified titanium dioxide nanotubes before and after exposure to ultraviolet radiation.

Nitric oxide release from the diazeniumdiolate-modified titanium dioxide nanotubes was stimulated by ultraviolet radiation provided from a 450 W mercury arc lamp. FIG. 5 shows illustrative comparative FTIR spectra of diazeniumdiolate-modified titanium dioxide nanotubes before and after exposure to ultraviolet radiation. The band centered at 1387 $cm^{-1}$ in spectrum 20 is characteristic of the diazeniumdiolate moiety. This band disappeared in spectrum 21 as a result of NO release. The released NO concentration after 15 hours of irradiation was up to 0.172 mmol NO per 50 mg of diazeniumdiolate-modified titanium dioxide nanotubes. The diazeniumdiolate-modified titanium dioxide nanotubes of this example did not contain deposited PbS quantum dots. However, the quantum dots could be added in a manner similar to that described in Example 2 to lower the band gap from the ultraviolet region to the visible or near-infrared region of the electromagnetic spectrum (see Example 4).

Example 4

Synthesis and NO Release of S-Nitrosothiol-Modified Titanium Dioxide Nanotubes

Figure 6:
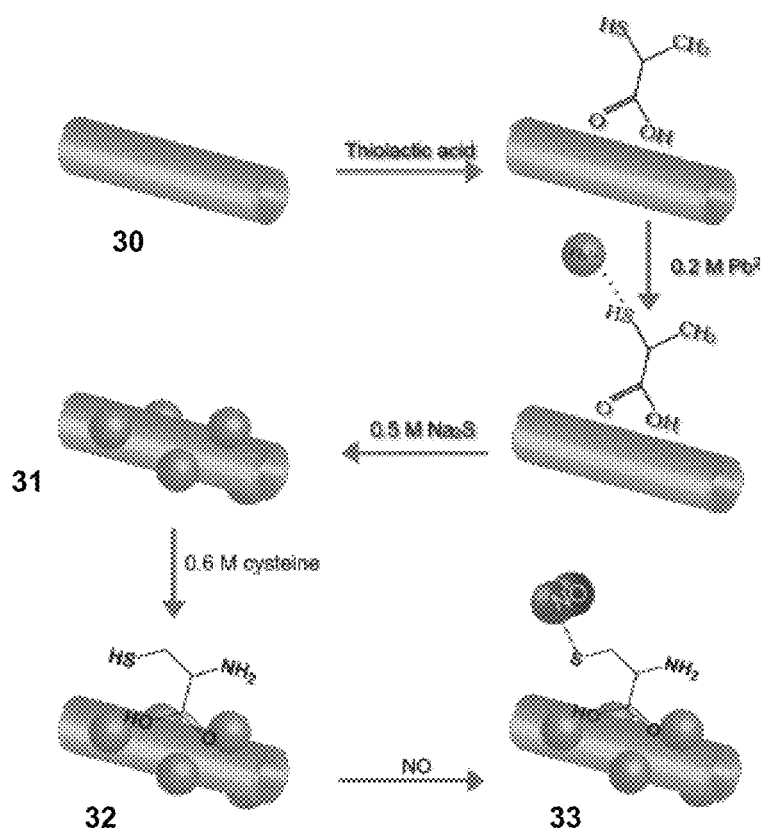
FIG. 6 shows a schematic of an illustrative synthesis of S-nitrosothiol-modified titanium dioxide nanotubes containing PbS quantum dots.

Thiols are believed to be involved in binding and metabolism of NO in vivo, and it has been shown that model systems such as N-acetylcysteine and glutathione bind and release NO photochemically. These and other carboxyl-containing thiols can be deposited on the titanium dioxide nanotubes through their carboxyl group. FIG. 6 shows a schematic of an illustrative synthesis of S-nitrosothiol-modified titanium dioxide nanotubes containing PbS quantum dots. As shown in FIG. 6, titanium dioxide nanotubes 30 were treated with thiolactic acid, $Pb^{2+}$ and PbS to form PbS quantum dots deposited on the titanium dioxide nanotubes by following the procedure outlined in Example 2. PbS quantum dot titanium dioxide nanotube 31 was then treated with cysteine to form thiol-modified titanium dioxide nanotube 32 in which the cysteine is adsorbed to the titanium dioxide nanotube through its carboxyl group. Exposure of thiol-modified titanium dioxide nanotube 32 to NO gas at 60 psi for 24 hours resulted in formation of S-nitrosothiol-modified titanium dioxide nanotube 33. Alternatively, the thiol could be reacted with sodium nitrite in HCl solution to form the S-nitrosothiol.

Figure 7:
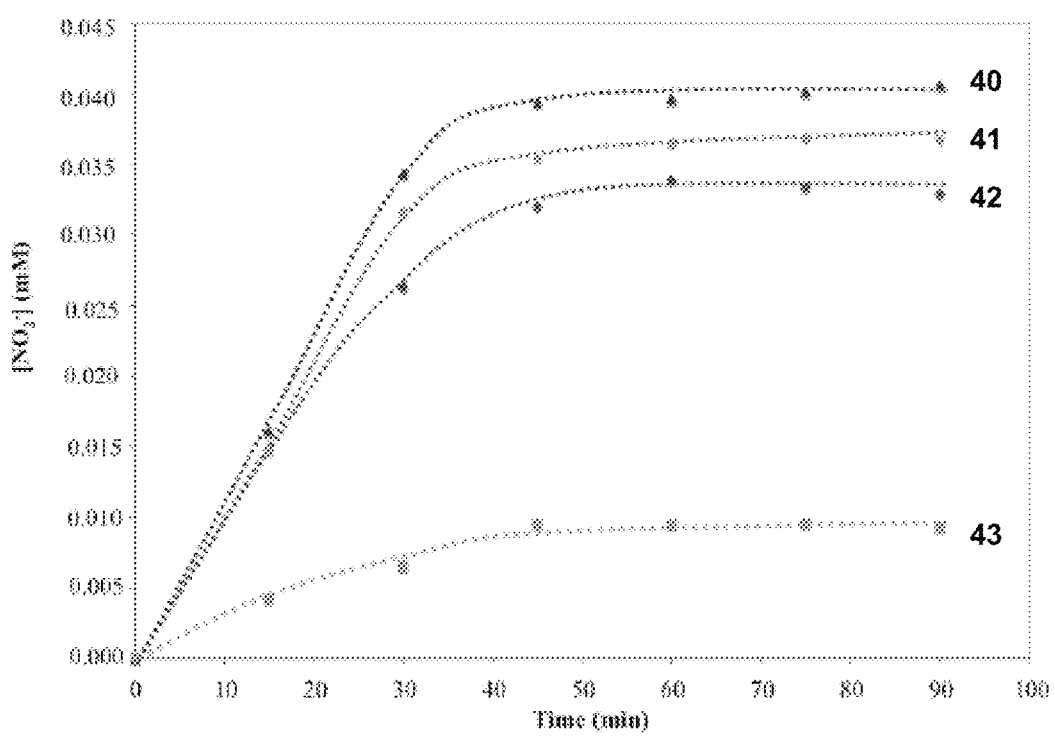
FIG. 7 shows a plot of near-infrared photochemical release of NO versus time for 5-nitrosothiol-modified titanium dioxide nanotubes both before and after purification by filtration.

The S-nitrosothiol-modified titanium dioxide nanotubes 33 released NO upon exposure to near infrared electromagnetic radiation using a Ray-Sorb filter. FIG. 7 shows a plot of near-infrared photochemical release of NO versus time for S-nitrosothiol-modified titanium dioxide nanotubes both before and after purification by filtration. Comparative data for S-nitrosothiol-modified titanium dioxide nanotubes not containing PbS quantum dots is also presented for purposes of comparison. As shown in FIG. 7, curves 40 and 41 indicated that 5-nitrosothiol-modified titanium dioxide nanotubes released NO upon exposure to near-infrared electromagnetic radiation both before (41) and after (40) purification. In contrast, 5-nitrosothiol-modified titanium dioxide nanotubes not containing PbS quantum dots only appreciably released NO before purification by filtration (curve 42) but not after purification (curve 43). The difference in NO release between curves 42 and 43 can be attributed to physical adsorption of NO by the titanium dioxide nanotubes during S-nitrosothiol formation. This adsorbed NO is weakly bound and released even in the dark. As shown in FIG. 7, adsorbed NO was not fully removed from S-nitrosothiol-modified titanium dioxide nanotubes not containing PbS quantum dots before purification, as evidenced by the strong NO release in curve 42. In contrast, strong NO release was maintained in S-nitrosothiol-modified titanium dioxide nanotubes containing Pbs quantum dots both before and after purification, as evidenced by strong NO release in both curves 40 and 41.

Example 5

Synthesis Metal Complex-Modified Titanium Dioxide Nanotubes

Titanium dioxide nanotubes were functionalized with an organosilane linker species following the procedure set forth in Example 3. In the present example, however, the organosilane contained a ligand donor, such as imidazole or pyridine, which is operable for coordinating a metal complex. Following organosilane attachment, a metal nitrosyl complex was coordinated to the ligand donor attached to the titanium dioxide nanotubes. Ruthenium nitrosyl complexes are among the best studied metal nitrosyl complexes, and a ruthenium salen nitrosyl complex was used in the present example.

Example 6

Polymer Wrapping of Titanium Dioxide Nanotubes

Figure 8A:
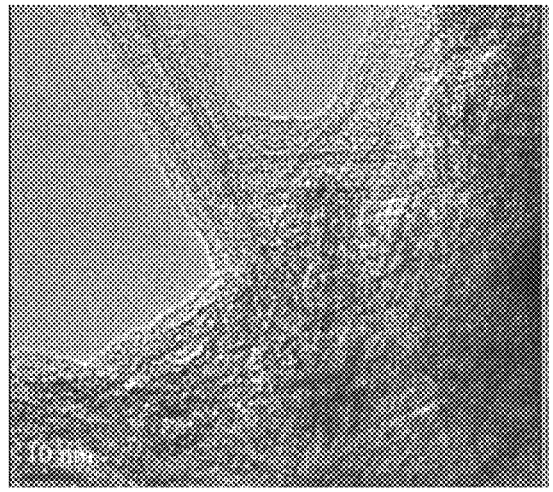
FIGS. 8A and 8B show illustrative TEM images of titanium dioxide nanotubes wrapped with poly-L-arginine.
Figure 8B:
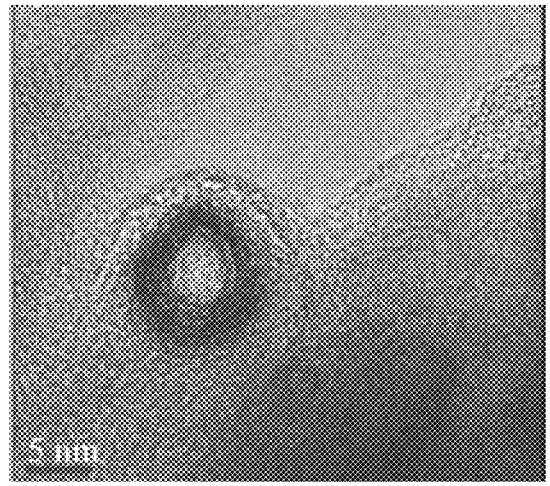

Poly-L-arginine was mixed with a solution of functionalized titanium dioxide nanotubes. FIGS. 8A and 8B show illustrative TEM images of titanium dioxide nanotubes wrapped with poly-L-arginine. FIG. 8A presents a side view TEM image, and FIG. 8B presents a top view TEM image. As shown in the TEM images, the titanium dioxide nanotubes were well wrapped by the water-soluble polymer.

Example 7

Imaging Titanium Dioxide Nanotubes In Vivo and In Vitro

Figure 9:
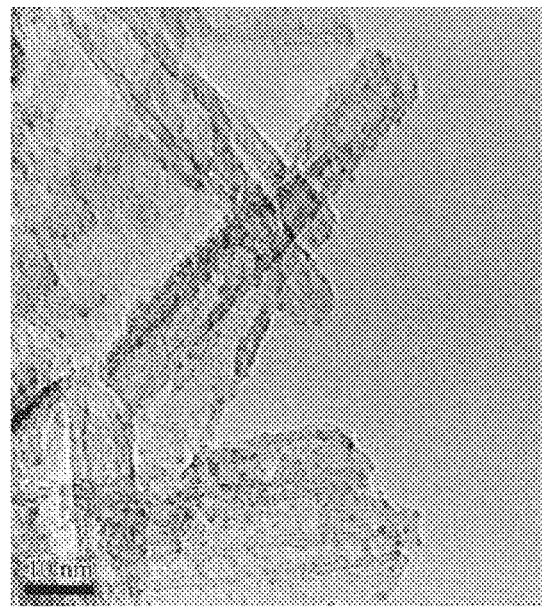
FIG. 9 shows an illustrative TEM image of Au nanoparticles deposited on titanium dioxide nanotubes.
Figure 10:
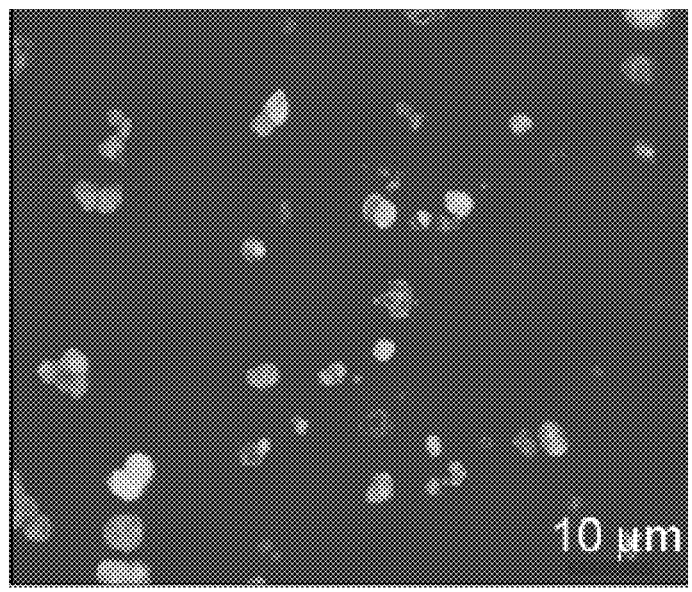
FIG. 10 shows an illustrative confocal microscopy image of Au nanoparticles deposited on titanium dioxide nanotubes after wrapping in poly-L-arginine.

Gold nanoparticles attached to the titanium dioxide nanotubes were used to image the titanium dioxide nanotubes in vivo and in vitro. Such gold nanoparticles are known to emit in the near infrared region of the electromagnetic spectrum, and such emissions are transparent to human tissue. A modification of Example 2 was used to attach gold nanoparticles to the titanium dioxide nanotubes. After depositing thiolactic acid on the titanium dioxide nanotubes, $Au^{2+}$ was coordinated to the thiol moiety. Thereafter, a solution of $HAuCl_4$ was used to produce Au nanoparticles with an average particle size of 1.6±0.2 nm. FIG. 9 shows an illustrative TEM image of Au nanoparticles deposited on titanium dioxide nanotubes. FIG. 10 shows an illustrative confocal microscopy image of Au nanoparticles deposited on titanium dioxide nanotubes after wrapping in poly-L-arginine.

From the foregoing description, one of ordinary skill in the art can easily ascertain the essential characteristics of this disclosure, and without departing from the spirit and scope thereof, can make various changes and modifications to adapt the disclosure to various usages and conditions. The embodiments described hereinabove are meant to be illustrative only and should not be taken as limiting of the scope of the disclosure, which is defined in the following claims.

What is claimed is the following:

1. A composition for release of nitric oxide under photochemical conditions, comprising annealed titanium dioxide nanotubes, said titanium dioxide nanotubes having a nitric oxide-releasing compound deposited on the titanium dioxide nanotubes with a organosilane linker and a semiconductor material covalently attached inside of said titanium dioxide nanotubes, wherein the semiconductor material comprises a quantum dot material selected from the group consisting of PbS, PbSe, CuS, $Cu_2S$, $FeS_2$, CdS, CdSe, CdTe, ZnS, $Ag_2S$, $CuInS_7$, $Rh_2S_3$ and $RuS_2$ and the nitric oxide-releasing compound is selected from the group consisting of diazeniumdiolate, a S-nitrosothiol and a metal nitrosyl complex and releases nitric oxide upon exposure to photochemical radiation of 700 nm to 1400 nm.

2. The composition of claim 1, wherein the semiconductor material is PbS.

3. The composition of claim 1, wherein a portion of the semiconductor material is also deposited on the exterior surface of the titanium dioxide nanotubes.

4. The composition of claim 1, wherein at least a portion of the nitric oxide-releasing compound is deposited on the exterior surface of the titanium dioxide nanotubes.

5. The composition of claim 1, further comprising:
a polymer wrapping the titanium dioxide nanotubes.

6. The composition of claim 1, wherein the polymer is a water-soluble polymer.

7. The composition according to claim 1, said composition further comprising tissue-targeting moieties deposited on the exterior surface of the titanium dioxide nanotubes.

8. The composition according to claim 7, wherein said tissue targeting moieties are antibodies, peptides, DNA or RNA.

9. The composition according to claim 8, wherein said tissue targeting moieties are antibodies.

* * * * *